US008101403B2

(12) United States Patent
Yager et al.

(10) Patent No.: US 8,101,403 B2
(45) Date of Patent: Jan. 24, 2012

(54) METHOD AND DEVICE FOR RAPID PARALLEL MICROFLUIDIC MOLECULAR AFFINITY ASSAYS

(75) Inventors: Paul Yager, Seattle, WA (US); Turgut Fettah Kosar, Cambridge, MA (US); Michael Wai-Haung Look, Seattle, WA (US); Afshin Mashadi-Hossein, Bellevue, WA (US); Katherine McKenzie, Seattle, WA (US); Kjell E. Nelson, Seattle, WA (US); Paolo Spicar-Mihalic, Seattle, WA (US); Dean Y. Stevens, Seattle, WA (US); Rahber Thariani, Seattle, WA (US)

(73) Assignee: University of Washington, Seattle, WA (US)

( * ) Notice: Subject to any disclaimer, the term of this patent is extended or adjusted under 35 U.S.C. 154(b) by 304 days.

(21) Appl. No.: 12/444,385

(22) PCT Filed: Oct. 4, 2007

(86) PCT No.: PCT/US2007/080479

§ 371 (c)(1),
(2), (4) Date: Apr. 3, 2009

(87) PCT Pub. No.: WO2008/043041

PCT Pub. Date: Apr. 10, 2008

(65) Prior Publication Data

US 2010/0081216 A1 Apr. 1, 2010

Related U.S. Application Data

(60) Provisional application No. 60/828,127, filed on Oct. 4, 2006.

(51) Int. Cl.
*C12M 1/34* (2006.01)

(52) U.S. Cl. ....... 435/287.2; 427/2.11; 435/4; 435/6.11; 435/7.1; 435/286.5; 436/518; 436/524; 436/536

(58) Field of Classification Search ........................ None
See application file for complete search history.

(56) References Cited

U.S. PATENT DOCUMENTS

| | | | |
|---|---|---|---|
| 5,112,739 | A | 5/1992 | Meneghini et al. |
| 5,716,852 | A | 2/1998 | Yager et al. |
| 5,972,710 | A | 10/1999 | Weigl et al. |
| 5,994,150 | A | 11/1999 | Challener et al. |
| 6,007,775 | A | 12/1999 | Yager |
| 6,159,739 | A | 12/2000 | Weigl |
| 6,207,369 | B1 | 3/2001 | Wohlstadter et al. |

(Continued)

FOREIGN PATENT DOCUMENTS

KR 10-1999-0036069 5/1999

(Continued)

OTHER PUBLICATIONS

U.S. Appl. No. 11/939,292, filed Nov. 13, 2007, Yager et al.

(Continued)

*Primary Examiner* — N. Yang

(74) *Attorney, Agent, or Firm* — Karen S. Canady; canady + lortz LLP

(57) ABSTRACT

Disclosed are methods and devices for rapid parallel molecular affinity assays performed in a microfluidic environment. The invention exploits hydrodynamic addressing to provide simultaneous performance of multiple assays in parallel using a minimal sample volume flowing through a single channel.

22 Claims, 12 Drawing Sheets

U.S. PATENT DOCUMENTS

| | | | |
|---|---|---|---|
| 6,221,677 B1 | 4/2001 | Wu et al. | |
| 6,227,641 B1 | 5/2001 | Nishikori | |
| 6,268,125 B1 | 7/2001 | Perkins | |
| 6,454,945 B1 | 9/2002 | Weigl | |
| 6,541,213 B1 | 4/2003 | Weigl | |
| 6,664,104 B2 | 12/2003 | Pourahamadi et al. | |
| 7,258,837 B2 | 8/2007 | Yager | |
| 7,271,007 B2 | 9/2007 | Weigl | |
| 7,550,267 B2 | 6/2009 | Hawkins et al. | |
| 2002/0037499 A1* | 3/2002 | Quake et al. | 435/5 |
| 2004/0096960 A1* | 5/2004 | Burd Mehta et al. | 435/287.2 |
| 2004/0256230 A1 | 12/2004 | Yager et al. | |
| 2006/0166375 A1 | 7/2006 | Hawkins et al. | |
| 2007/0042427 A1 | 2/2007 | Gerdes et al. | |
| 2008/0014575 A1 | 1/2008 | Nelson | |
| 2009/0068760 A1 | 3/2009 | Nelson et al. | |

FOREIGN PATENT DOCUMENTS

WO WO/9706437 2/1997

OTHER PUBLICATIONS

Dittrich et al. (2006) "Micro total analysis systems. latest advancements and trends", *Analytical Chemistry* 78(12): 3887-3908.

Foley et al. (2007) "Concentration gradient immunoassay II. computational modeling for analysis and optimization" *Analytical Chemistry* 79(10): 3549-3553 (NIH Manuscript 12pp).

Kusterbeck et al. (1998) "Field demonstration of a portable flow immunosensor" *Field Analytical Chemistry and Technology* 2(6):341-350.

Nelson et al. (2007) "Concentration gradient immunoassay I. an immunoassay based on interdiffusion . . . microchannel" *Analytical Chemistry* 79(10): 3542-3548 (NIH Manuscript 27pp).

PCT International Search Report and Written Opinion (ISA:KIPO) for corresponding PCT Patent Application Application No. PCT/US2007/080479 filed on Oct. 4, 2007.

Product brochure, Micronics: microflow system, *Micronics* 2003, Doc No. 700031-01 Rev A—Apr. 2003, 5pp.

Rabbany et al. (1998) "A membrane-based displacement flow immunoassay" *Biosensors & Bioelectronics* 13: 939-944.

Yager et al. (2006) "Microfluidic diagnostic technologies for global public health" *Nature* 442(7101): 412-418.

Zimmerman et al. (2005) "Modeling and optimization of high-sensitivity, low-volume microfluidic-based surface immunoassays" *Biomedical Microdevices* 7(2): 99-110.

* cited by examiner

Schematic Immunoassay Operation

Step 1: Buffer wet out

- Close valves 2 and 3, open 1 and 4.
- Pump buffer from right (valve 4 to valve 1) to wet out both membranes
- Close valve at left and stop pumping

Figure 5

Step 2 (v1): Load sample

- With valves 1 and 2 closed, pump in sample from right, which exits below the membrane.
- No flow over 2° Ab membrane, which do not diffuse away because of high molecular weight

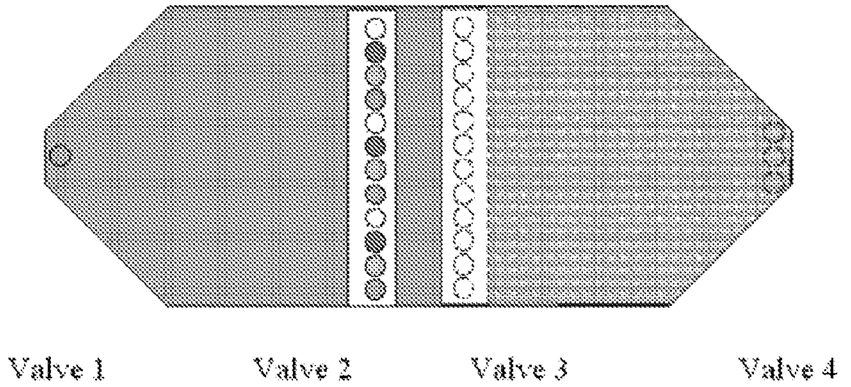

Step 2 (v2): Load sample and control solutions

- With valves 1 and 2 closed, pump in three solutions: sample, positive control (solution with all analytes at high levels), and negative control (solution with no sample antigens)
- No flow over 2° Ab membrane, which do not diffuse away because of high molecular weight

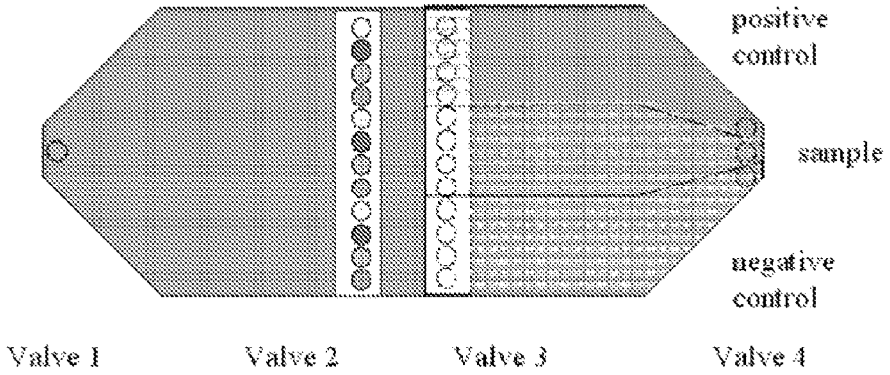

Figure 6

Figure 7
Step 3: Rinse
- Rinse with buffer (valves 1, 2 closed, 3 and 4 open) to remove excess sample from membrane
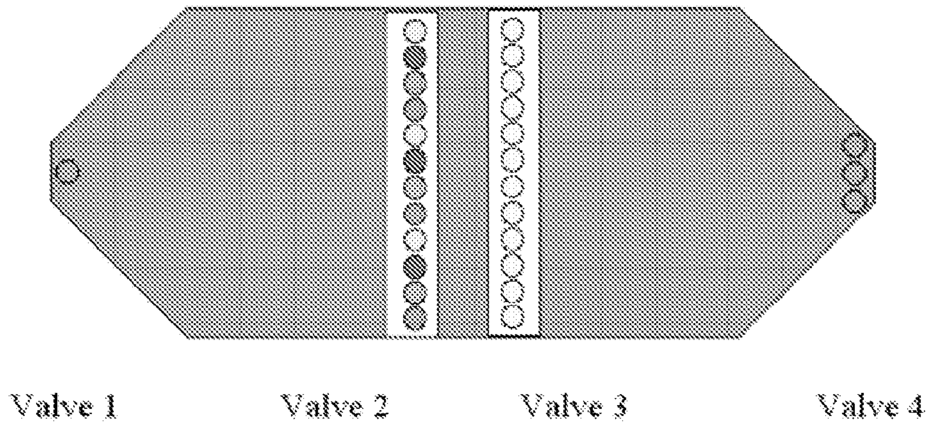
Step 4: load 2° Abs onto capture zones
- Close valves 1 and 4, pump buffer from valve 2 to 3, pushing 2° Ab from left membrane through the one at the right
- Continue until sufficient secondary Ab is transferred to capture zones.
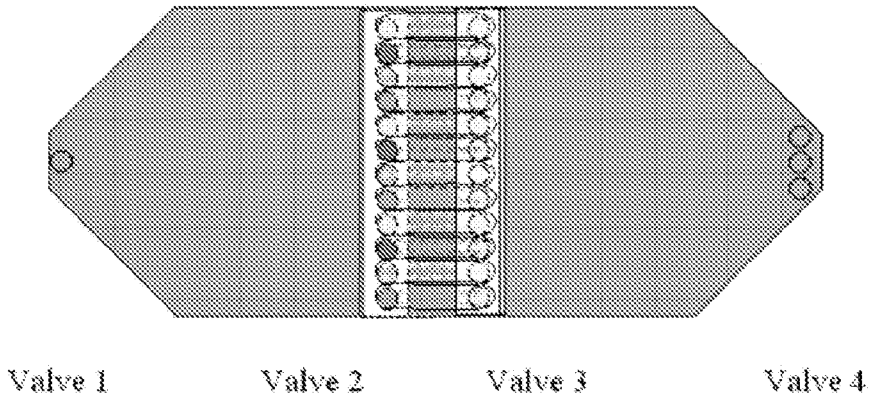
Figure 8

Step 5: rinse away excess 2° Ab

- Using fluids from either valve 1 or 2, (with valve 3 open and 4 closed) flush until all excess secondary Ab is pushed through capture membrane
- DETECT (if this is Au-labeled Ab, for example) by measuring optical density of spots
- Assay complete

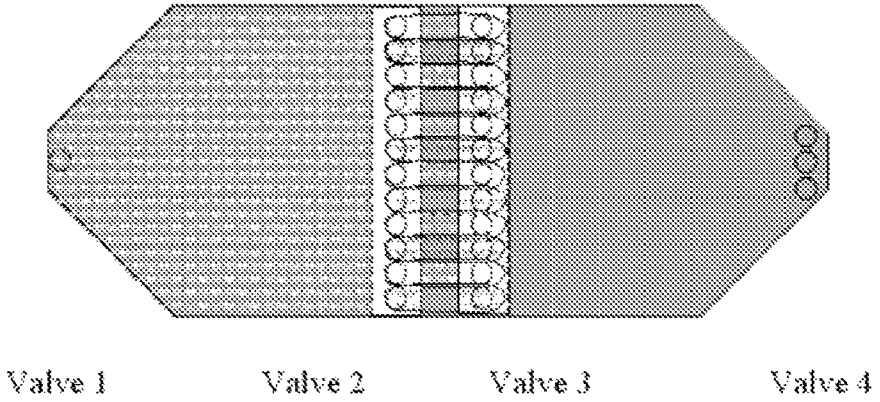

Figure 9

Step 6*: Add secondary reagent, incubate and image

- Pump secondary reagent from right at slow rate
- Positive controls and positive sample spots darken over a few seconds to minutes

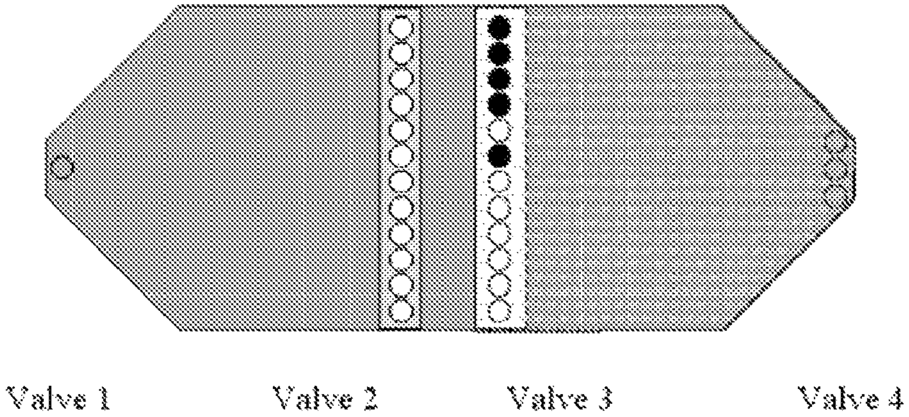

Figure 10

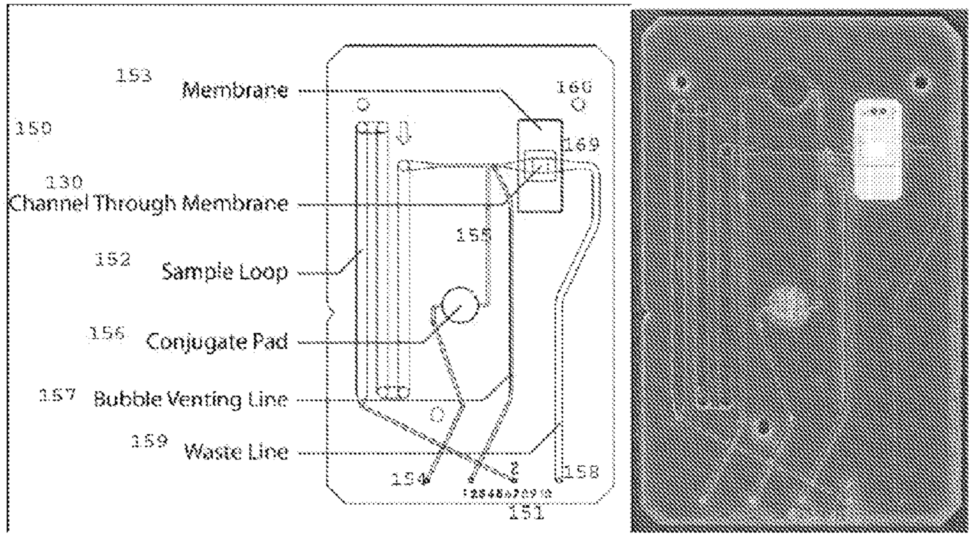
Figure 15A-B
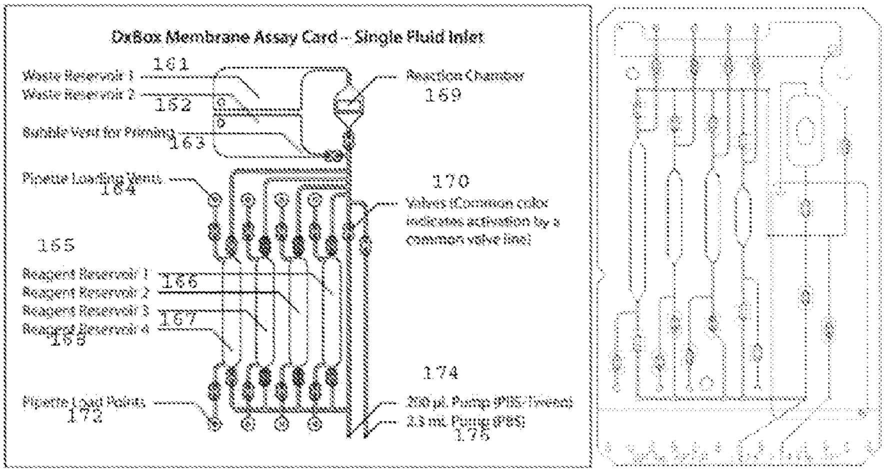
Figure 16A-B

METHOD AND DEVICE FOR RAPID PARALLEL MICROFLUIDIC MOLECULAR AFFINITY ASSAYS

This application claims the benefit of U.S. provisional patent application No. 60/828,127, filed Oct. 4, 2006, the entire contents of which are incorporated herein by reference.

TECHNICAL FIELD OF THE INVENTION

This invention relates generally to methods and devices for rapid parallel molecular affinity assays performed in a microfluidic environment. The invention exploits hydrodynamic addressing to provide simultaneous performance of multiple assays in parallel using a minimal sample volume flowing through a single channel.

BACKGROUND OF THE INVENTION

Immunoassays take advantage of the specific binding abilities of antibodies to be widely used in selective and sensitive measurement of small and large molecular analytes in complex samples. The driving force behind developing new immunological assays is the constant need for simpler, more rapid, and less expensive ways to analyze the components of complex sample mixtures. Current uses of immunoassays include therapeutic drug monitoring, screening for disease or infection with molecular markers, screening for toxic substances and illicit drugs, and monitoring for environmental contaminants.

Some assays have made use of laminar flow and diffusion profiles of analytes complexed with binding particles (see, e.g., U.S. Pat. No. 6,541,213 and U.S. Patent Application 2006/0166375, published Jul. 26, 2006). Such assays, however, are limited by their inability to provide for detection of multiple analytes in a single sample and in a single fluidic channel.

There remains a need for a device that allows for simultaneous performance of dozens of immunoassays in a minimum of time using a minimum of sample volume and in a minimal space. The invention described herein meets these needs and more through the use of hydrodynamic addressing and parallel flow.

SUMMARY OF THE INVENTION

The invention provides a method and assay device for detection of an analyte in a fluidic sample. In one embodiment, the device comprises:

(a) a microfluidic chamber having a first inlet;

(b) a first surface in communication with the first inlet, wherein the first surface comprises a plurality of capture regions;

(c) a plurality of capture agents immobilized on the capture regions, wherein the capture agents specifically bind the analyte;

(d) a reagent storage depot in communication via a single fluidic channel with the first surface, wherein the storage depot comprises a plurality of reagent regions; and, (e) a plurality of detection reagents that specifically bind the analyte and that become mobile upon contact with fluid, wherein the detection reagents are disposed within the reagent regions.

The first surface can comprise a porous carrier, such as a membrane or other porous structure, a flat surface, or other structure to which the capture agents can be immobilized while retaining the ability to be brought into contact with analytes delivered via fluid passing over the first surface.

The reagent storage depot can comprise one or more cavities, and/or a polymeric compound immobilized on the device. The storage depot is provided by stabilizing the reagents in a solid state using, for example, a porous matrix (e.g., a polymer, gel or soluble salt) that either swells on contact with the fluid and releases the reagents or completely dissolves thereby delivering the reagent. The storage depot can also be provided by locating the detection reagents, in dry form, in physical cavities, such that contact with fluid mobilizes the reagents. In each embodiment, the reagent(s) is immobile in its dry form and becomes mobilized upon contact with fluid such that the reagent is delivered, upon mobilization, to the first surface where it can react with the captured analyte.

In one embodiment, the storage depot comprises a porous membrane that is aligned parallel to the first surface. The device is well-suited to an embodiment having a first surface in which the plurality of capture regions are arranged linearly and perpendicular to the long axis of the single fluidic channel that provides communication between the storage depot and the first surface. The reagent regions are likewise arranged linearly and perpendicular to the long axis of the single fluidic channel, such that the linear arrangement of reagent regions is parallel to the linear arrangement of capture regions. As fluid traverses the single fluidic channel, flowing from the storage depot to the first surface, reagents are mobilized in the reagent regions and flow to the capture regions. The flow conditions of the channel are such that differing reagents disposed on the reagent regions travel in parallel to corresponding capture regions.

The device typically comprises a plurality of polymeric layers. The polymeric layers can be used to devise the configuration of inlets, channels, cavities and surfaces suitable for a particular embodiment. In some embodiments of the device, for example, a second inlet is provided in communication with the storage depot. The second inlet can be used to deliver fluid to effect mobilization of the reagents stored in the storage depot. Alternatively, the same fluid stream that delivers analyte to the first surface can also serve to effect mobilization of the reagents stored in the storage depot.

In another embodiment, an outlet is provided in communication with the first surface. Such an outlet can be used, for example, to draw fluid away from the first surface if desired. Those skilled in the art can appreciate that the outlet allows one to analyze the effluent or to draw off excess fluid prior to delivery of a subsequent fluid stream, in addition to other uses.

The device can further comprise one or more channels that provide communication between the first inlet and the first surface and/or between the second inlet and the storage depot. In one embodiment, 3 channels provide communication between the first inlet and the first surface. Multiple channels from the inlet to the first surface, for example, can be used to deliver multiple analytes, or, in a typical embodiment, three channels are used to deliver one analyte sample and two control samples (e.g., positive and negative controls).

The invention further provides a method of detecting the presence of an analyte in a fluidic sample. The method typically comprises;

(a) delivering a fluidic sample into the first inlet of a device of claim 1 under conditions permitting contact between the sample and the capture agents immobilized on the first surface;

(b) contacting a single stream of fluid with the plurality of detection reagents under conditions effecting migration of the detection reagents to the first surface;

(c) detecting the presence of detection reagent bound to analyte that is bound to the immobilized capture agents, whereby presence of detection reagent is indicative of the presence of the analyte.

In a typical embodiment, the delivering of step (a) comprises pumping the fluidic sample into the first inlet. The method can further comprise delivering one or more control samples via laminar flow into the first inlet. Where controls are desired, step (a) comprises delivering one stream of a test fluidic sample, one stream of a positive control fluidic sample, and one stream of a negative control fluidic sample. In one embodiment, the streams of fluidic sample are delivered via a single channel. In another embodiment, the streams of fluidic sample are delivered via separate channels. For example, a 3-channel embodiment can deliver test sample, positive control sample and negative control sample, each via a separate channel. Alternatively, the 3 streams can be delivered in one channel using controlled fluid pumping to avoid mixing of streams.

In one embodiment, the contacting of step (b) comprises pumping fluid into a second inlet that is in communication with the reagent storage depot. The fluid is typically a buffer and serves to mobilize the reagent so that it can contact and bind analyte that has been immobilized on the first surface upon binding capture agent. Those skilled in the art understand that rinsing or washes can be used to clear out unbound reagents between steps of the method.

In some embodiments, the delivering of step (a) provides the contacting of step (b), whereby the fluidic sample, upon contact with the detection reagents, effects migration of the detection reagents. In other words, steps (a) and (b) can be accomplished with a single stream of fluidic sample. Those skilled in the art can appreciate design arrangements for the device that would facilitate implementation of such an embodiment. For example, the reagent regions can be positioned between the first inlet and the capture regions.

In a typical embodiment, the capture agents and the detection reagents comprise antibodies and/or antigens. In some embodiments, the contacting of step (b) further comprises delivering to the first surface an amplification reagent that binds to the detection reagents. The detection reagents are labeled, either directly or indirectly, and the detectable signal can be provided or amplified using known techniques and materials.

Detection of signal can be achieved by a variety of means known in the art, including but not limited to, measuring an optical property such as optical absorbance, reflectivity, optical transmission, chemiluminescence or fluorescence. In some embodiments, signal can be detected by eye. Optical readers are preferred when a quantitative measurement is desired.

BRIEF DESCRIPTION OF THE DRAWINGS

FIG. 5: First version of sample load. In version 1, step 2 comprises pumping in sample from the right, with valves 1 and 2 closed. Sample exits below the membrane via an outlet not shown here. No flow over the secondary antibody membrane, which antibodies do not diffuse away because of high molecular weight.

FIG. 6: Illustration of how, in the second version of the sample load, everything is the same as in the previous version, except that laminar flow is used to flow 2 or 3 different solutions across the capture reagent membrane. With valves 1 and 2 dosed, three solutions are pumped in: sample, positive control (all analytes at high levels), and negative control (no sample antigens). No flow over the secondary antibody membrane, which antibodies do not diffuse away because of high molecular weight.

FIG. 7: Illustrates the rinse. Valves 1 and 2 are closed; 3 and 4 are open. Rinse with buffer to remove excess sample from membrane.

FIG. 8: Illustrates the loading of secondary antibodies Close valves 1 and 4; pump buffer from valve 2 to 3, pushing 2 antibody from left membrane through the one at the right. Continue until sufficient 2 antibody is transferred to capture zones.

FIG. 9: Illustrates the rinsing of secondary antibodies. Using fluids from either valve 1 or 2 (with valve 3 open and 4 closed), flush until all excess secondary antibody is pushed through capture membrane. Detect of this is Au-labeled antibody, for example) by measuring optical density of spots. Assay is complete.

FIG. 10: Illustrates a detection step. This and further steps are only necessary if using an amplification step, Pump secondary reagent from right at slow rate. Positive controls and positive sample spots darken over a few seconds to minutes.

FIG. 15A-B: A self-contained microfluidic format, consisting of a laminate device in which connecting fluidic channels are formed, a membrane patterned with capture molecules, a porous pad containing dried detection reagent, and an external fluid-pumping and imaging system. The multiple fluid inlets are each fed by separate pumps in this preliminary design, sidestepping the need for valves. The device is pictured as a diagram (FIG. 15A) and photograph (FIG. 15B) of two revisions of the design.

FIG. 16A-B: Functional schematic (FIG. 16A) and CAD design (FIG. 16B) for as card with single fluid inlet to the reaction chamber (the location of the assay membrane).

OVERVIEW OF THE INVENTION

Figure 1A:
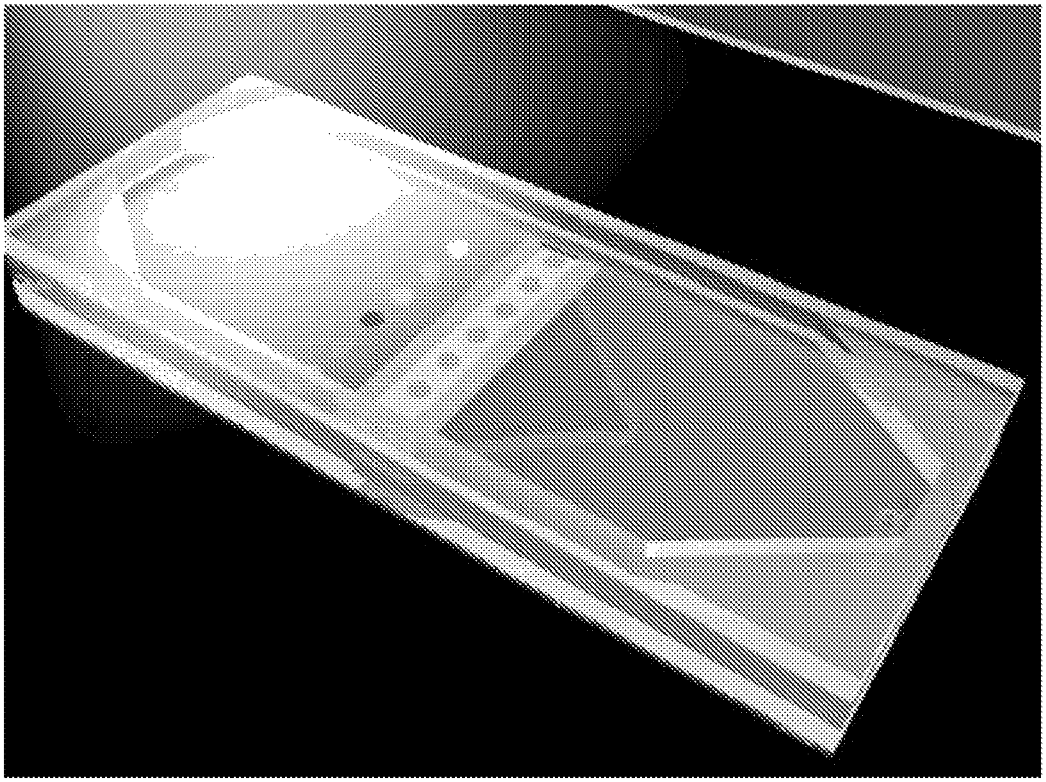
FIG. 1A: Schematic design of version 1 of the polymeric disposable in which the secondary reagents are contained within cavities in the disposable. Two sets of fluid inlets are located at the right and left ends of the disposable as well as a single outlet path below the embedded membrane (center), which is loaded with molecules.
Figure 1B:
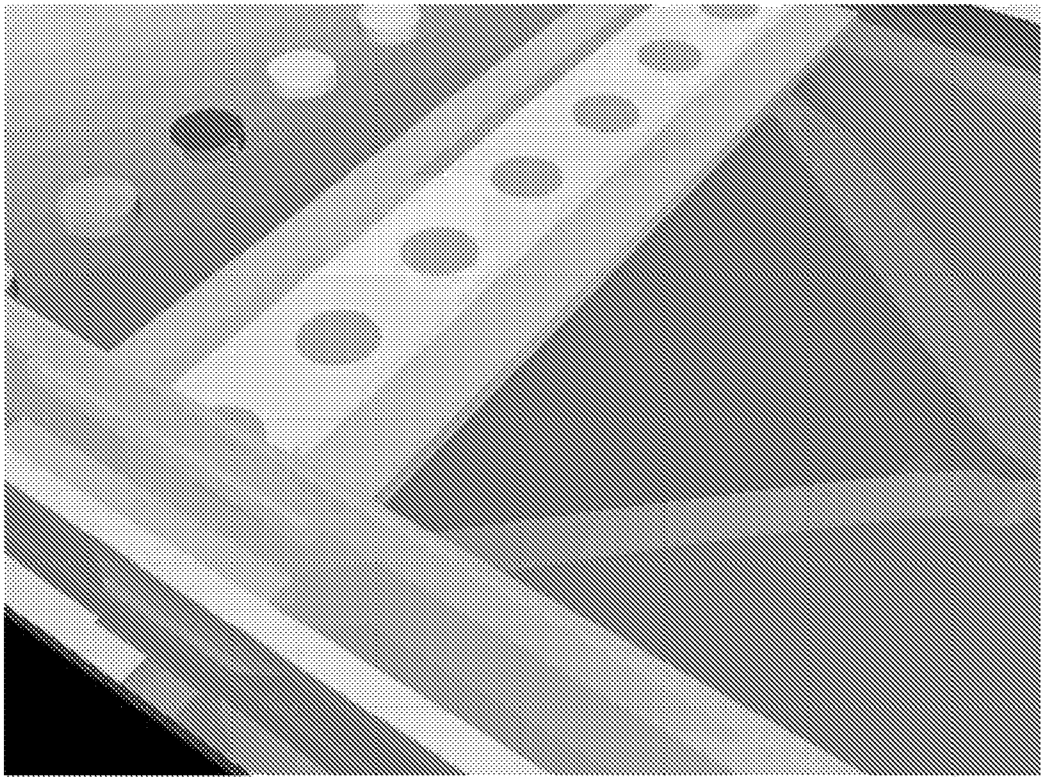
FIG. 1B: Close-up of the central portion of the same image as in FIG. 1A.
Figure 1C:
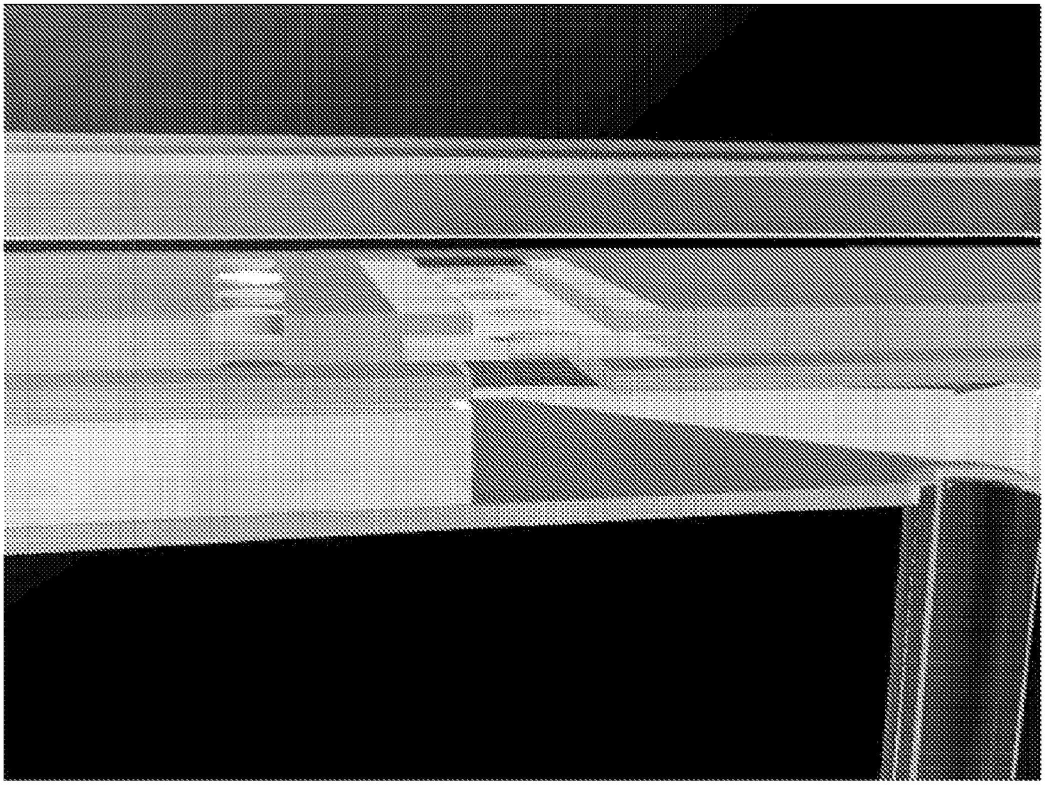
FIG. 1C: Cut-away view of the same device (central portion) as in FIGS. 1A and 1B, showing the relative locations of the different layers, the capture membrane and the secondary reagent depots. The exit port for the device is below the membrane, and fluid exits to the right.

The invention relates to a method and device for performing rapid molecular binding assays, including immunoassays, and in particular, sandwich immunoassays. The method involves binding a plurality of primary capture reagents to a plurality of locations on a porous membrane, placing a matched set of secondary (or detection) binding molecules in a line of cavities or on a porous membrane aligned parallel to the reagent storage locations, but separated by a gap, and a method for sandwiching the analyte in question between them using laminar flow in a microfluidic device. The sample is loaded onto the first membrane by pumping it through said first membrane, where sample analyte molecules become bound to the capture molecules immobilized on that membrane. Fluid is then pushed past the storage depot line or through the second membrane to release the secondary capture molecules and transport them to the first membrane to "sandwich" the analyte molecules. Detection is then possible by either directly (if the secondary capture molecule is directly observable (such as a fluorescently- or Au-labeled secondary antibody) or indirectly (using for example, secondary antibodies labeled with enzymes such as horseradish peroxidase (HRP) followed by flow over the first membrane of a solution producing an observable signal, such as precipitatable tetramethylbenzidine (TMB).

The device allows the simultaneous performance of dozens of immunoassays (as well as positive and negative control reactions) in a minimum of time using a minimum of sample volume and in a minimal space. Reading the results of the immunoassays may either be made directly (by eye), or with the aid or a quantitative optical reader. Conventional off-the-shelf reagents can be used to minimize cost. It is particularly well adapted for performance of multiple immunoassays on an inexpensive polymeric disposable device that may be read out directly or using an optical reader.

APPLICATIONS OF THE INVENTION

The invention disclosed herein is a design for a molecular binding assay (and a method of using that design). This assay system is well suited to use as the basis of immunoassays such as "sandwich immunoassays" Although the reagents and assays are referred to herein as immunoassay reagents and immunoassays, respectively, it is understood by those skilled in the art that a device that could perform any other assay (based on proteins, aptamers, nucleic acids, or other molecules) that involves molecules capable of binding to each other would fall under the scope of this invention.

In a typical embodiment of this assay, the device is fabricated from inexpensive polymeric components combined with porous membranes capable of binding to and immobilizing capture reagents such as capture immunoassays or target antigens, depending on the format of the immunoassay. The arrangement allows for storage of both capture reagents and secondary reagents in dry form on the polymeric microfluidic device, thereby creating a self-contained disposable that can be used with or without a reader technology. By allowing the storage of multiple reagents in parallel, the disposable can be made to perform multiple immunoassays in parallel, as well as perform measurements of multiple analyte concentrations in samples, positive control solutions, and negative control solutions simultaneously. The assay assumes laminar flow conditions in all components, and microfluidic dimensions.

The immunoassay format can be manufactured very inexpensively, such that a polymeric disposable is suitable for use in point-of-care assays. Optical detection methods (optical absorption, diffuse reflectance absorption, or fluorescence) are typically utilized, although other methods are not excluded. The assays can operate in a simple qualitative yes/no fashion, or in a quantitative manner (using, for example, a quantitative optical reader). Detection of the optical signal indicating the binding of the analyte can be performed in either of two well-understood ways: One version involves the use of an optically detectable secondary antibody, such as an antibody bound (covalently or noncovalently) to colored microspheres, fluorescent molecules or nanoparticles, or strongly absorbing dyes of nanoparticles (such as gold nanoparticles). In a more sensitive version, the assay is an ELISA assay, in which the secondary antibody is labeled with an enzyme, and the final step after binding of the secondary antibody to the analyte is exposure of the enzyme-loaded capture membrane with a "developing solution"; examples are to be taken from the list of all known ELISA systems, including any of several commercially available horseradish peroxidase/precipitating tetramethylbenzidine systems.

A likely application for such a disposable (with or without use of a quantitative reader) is a point-of-care immunoassay system for use in the developing world, although use as an inexpensive point-of-care diagnostic system is also possible. The disposable polymeric immunoassay system can be coupled to other types of assays in a single integrated device.

DETAILED DESCRIPTION OF SPECIFIC EMBODIMENTS OF THE INTENTION

Exemplary versions of the device are described. The first is shown in FIG. 1A.

The device can be fabricated from seven polymeric layers. A representative example of a multiple polymeric layered device is shown in FIG. 2.

Figure 2:
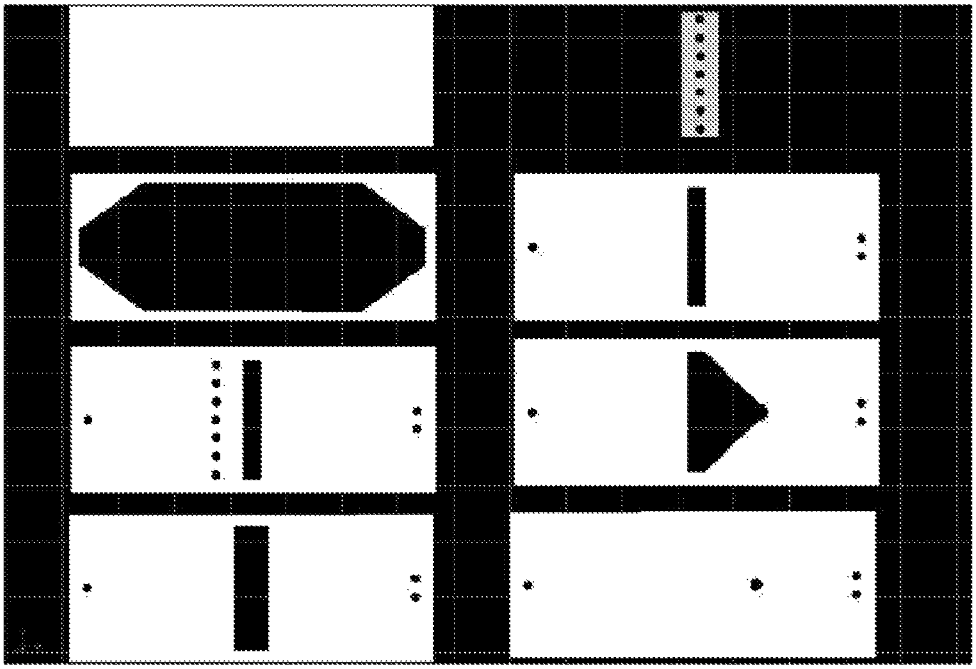
FIG. 2: Schematic of the minimal set of structural layers required to assemble version 1 of the immunoassay device.

A schematic of the minimal set of structural layers required to assemble version 1 of the immunoassay device (of FIG. 1A) is shown in FIG. 2. The layers are numbered in order of assembly, Layers 1, 4 and 8 are just C (carrier) layers (plain sheets of an appropriate polymer such as Mylar, PMMA, or others), whereas layers 2 and 7 are ACA (adhesive, carrier, adhesive) layers. Layers 3 and 6 are AC layers, with adhesive on one side that serve to seal layer 5, the membrane, in place. Layer 1 is the top cover of the device, and must consist of a clear (optically transparent) material to allow optical observation of the layer 5. Layer 2 is the main fluid cavity. Layer 3 is the "floor" of the main fluid cavity, which contains a (here large and rectangular) hole for fluid outflow, as well as a multiplicity of storage depots for storage of secondary reagents. These secondary reagents can be placed into the storage depots as one of the last steps of assembly of the polymeric device. Layer 4 is the cavity that localizes the permeable membrane. Layer 5 consists of a permeable membrane onto which capture molecules are immobilized prior to final assembly of the device, and which is placed within the rectangular cavity in layer 4. The deposition of the different capture molecules onto layer 5 can be in any form, but are shown here as circular spots. Layer 6 supports the permeable membrane. Layer 7 collects all flow through the membrane to a single port. Layer 8 is the floor of the device and couples to inlets and outlets for the device. Note that, in this schematic, the right side of all layers (but 5) are shown with two holes. In the schematic below either one hole or three are used, as explained below. Note that further embodiments of the device can be assembled in part using injection molded parts to reduce the part count and reduce fabrication costs.

Figure 3:
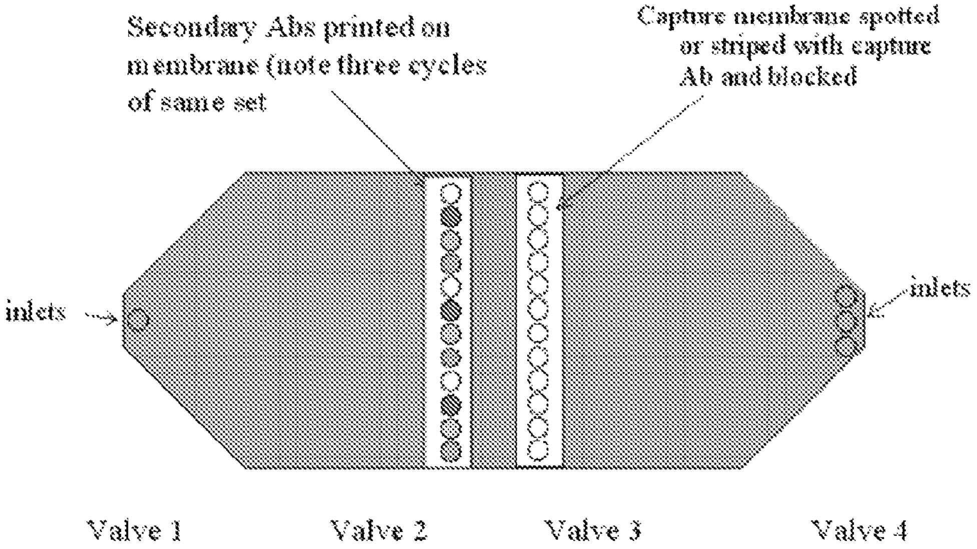
FIG. 3: Schematic of assembled immunoassay device with three inlet holes on the right, one on the left, and one outlet hole invisible below the porous membrane. Secondary antibodies are printed on a membrane (left column of dots) with three cycles of the same set. Capture membrane (right column of dots) is spotted or striped with capture antibody and blocked. The relative locations of 4 valves are indicated along the bottom of the figure.

Shown in FIG. 3 is an operation sequence for version 1 of the device as shown in FIGS. 1A and 2. In this schematic, the assembled device has three inlet holes on the right, one on the left, and one outlet hole invisible below the porous membrane. The cavity is designed in such a way that fluid entering the main cavity is "fully developed", and, therefore, flowing almost exclusively horizontally and at the same horizontal velocity top to bottom (as shown in this figure) by the time it reached either the membrane from the right, or the secondary reagent storage depots from the left.

Figure 4:
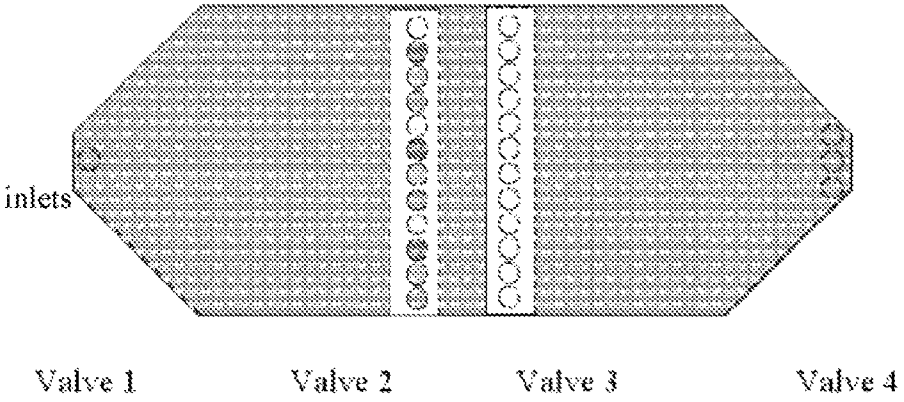
FIG. 4: Schematic illustration of how buffer is used to wet out the device from the right. Step 1 involves closing valves 2 and 3, opening valves 1 and 4, Buffer is pumped from the right (valve 4 to valve 1) to wet out both membranes. Valve at left is closed and pumping stopped.

As illustrated in FIG. 4, buffer is used to wet out the device from the right. Such a process proceeds with the exit below the device closed, so that almost all fluid flows from right to left. This wets the secondary reagent storage depots, necessitating that they begin to hydrate and dissolve. The high molecular weight of the secondary reagents prevents them from diffusing appreciably in the vertical direction (as shown in this figure) during the complete operation of the device. If it necessary to minimize vertical diffusion, the capping layer (layer 1 in FIG. 2) can be manufactured with fins that fit between the secondary reagent storage depots. The wet-out pushes minimum fluid through the membrane.

FIG. 5 illustrates a first version of sample load. In the simplest case, the valves "below" the left side of the device are closed and the sample is pumped in through a single inlet from the right, forcing the sample to flow through the semi-permeable membrane.

In the second version of the sample load (FIG. 6) everything is the same as in the previous version, except that laminar flow is used to flow 2 or 3 different solutions across the capture reagent membrane. One of these is the sample, but the other two are positive and negative controls (meaning solutions, presumably buffer, containing a high concentration of each analyte to be measured, and no analytes, respectively.) Under laminar flow conditions, only a controlled amount of interdiffusion between the streams occurs before they arrived at the capture membrane, and since flow then goes through the membrane, three distinct zones are maintained with respect to capture of analytes. This allows "real time calibration" of the immunoassay with a very simple format.

As shown in FIG. 7, in either case, buffer is flushed from the right (with the valve under the left side closed) to clear excess (free) analyte from the device and flush the capture membrane.

The secondary reagent (2° Ab, for example) is then loaded onto the analyte molecules that are bound to the capture membrane (via the capture molecules) by pumping buffer from the left inlet (with all the right inlet valves closed; see FIG. 8). This continues until all of the 2° Abs are transferred. Laminar flow (or channels or fins, if necessary) will ensure that the appropriate 2 Abs are transported to the appropriate capture molecule regions on the membrane.

The remaining 2° Ab is rinsed from the system to ensure that all capture zones receive equivalent doses of that reagent (FIG. 9). If a directly observable secondary reagent (such as a gold-labeled or fluorescently-labeled 2° Ab) is used, it is possible to observe and quantify the intensity of the observable signal on the appropriate locations of the capture membrane to measure analyte concentrations. If not, the detection method shown in FIG. 10 is used.

Assuming that an enzyme-labeled 2° Ab is used as the secondary reagent, a separate detection step is employed (FIG. 10). In this case the left-most valve is closed and a solution of a detection reagent is pumped from the right and through the membrane at a controlled rate. Spots then become observable as product built up. An example of a system that has proven useful in this regard is the horseradish peroxidase/precipitating tetramethylbenzidine system, although many other ELISA detection schemes have been demonstrated and could be used here. Those that produce a precipitated product are preferred because of the build-up of signal possible on the membrane over time and pushing of reagents through the membrane, but non-precipitating systems can also be used. Alternatively, other detection reagents can be stacked on top of the 2° Ab layer to produce strong signals using fluorescence or optical absorbance.

Figure 11:
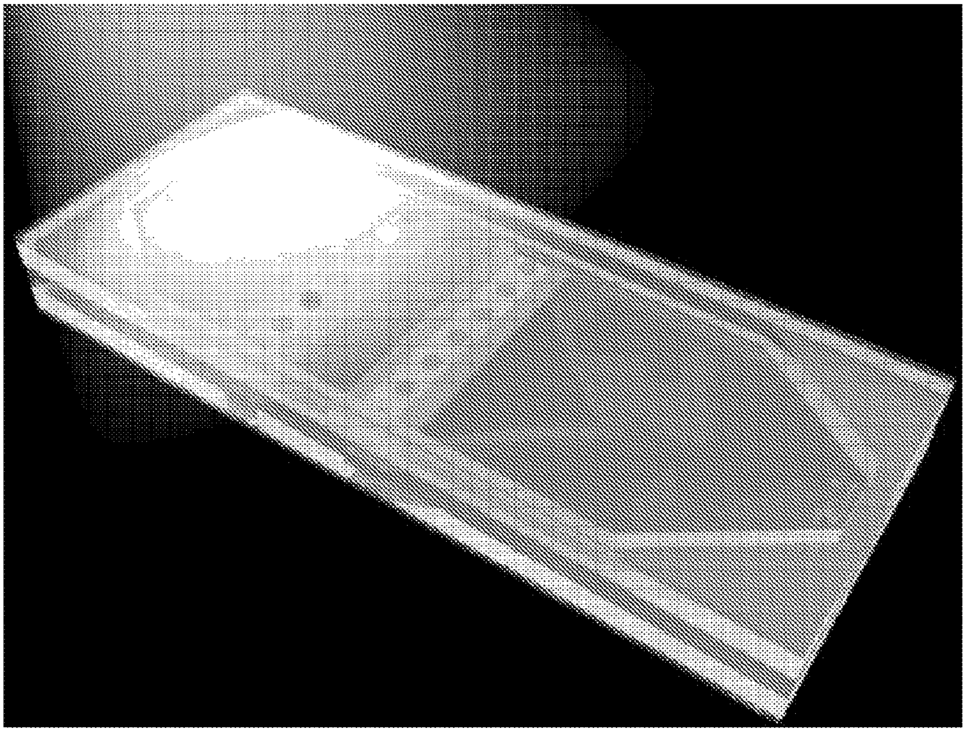
FIG. 11: Schematic of version 2 of the device and system.
Figure 12:
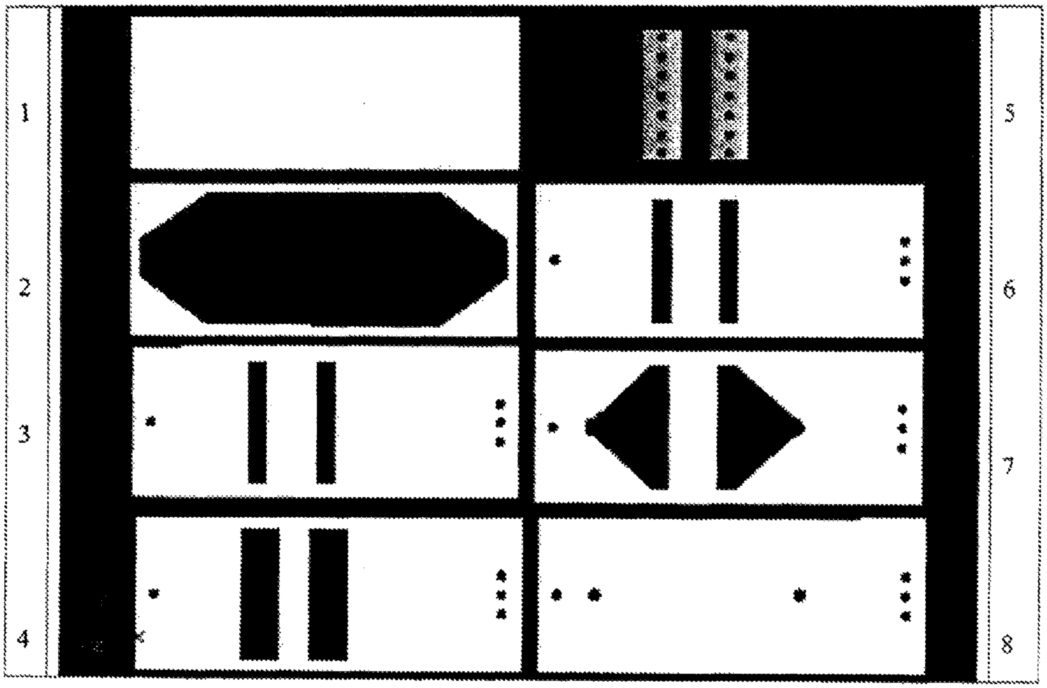
FIG. 12: Schematic of the minimal set of structural layers required to assemble version 2 of the immunoassay device as shown in FIG. 11.

The above-mentioned scheme relies on the deposition of the secondary reagents onto an impermeable surface to form depots for subsequent movement to the capture membrane. An alternative that allows the use of technology demonstrated in other types of assays is to use a second permeable membrane as the depot for the 2° Abs, allowing these reagents to be preloaded into a membrane before assembly of the card, and washed out of this membrane by flowing buffer up through the membrane. The preliminary design is shown in FIG. 11. This design allows all the reagents to be printed onto large sheets of membrane using commercial printing mechanisms for great simplification of manufacturing and, thereby, cost savings. Furthermore, the secondary reagent membrane can be prepared in the same way as the secondary reagents are in lateral flow immunoassay devices (immunochromatographic test strips).

Shown in FIG. 11 is a schematic of version 2 of the device and system; it is very similar to that shown in FIG. 1A, except that the 2° Ab storage is now on a permeable membrane that sits in a cavity like that for the capture membrane, there is a second channel below the second membrane (which is an inlet, not an outlet) and the 2° Ab spots are deposited (in a matrix of preserving chemicals) on the second membrane (at left). The second membrane is of a type with no or very low protein retention.

Schematic of the minimal set of structural layers required to assemble version 2 of the immunoassay device as shown in FIG. 11. The layers are numbered in order of assembly and have the same characteristics as those mentioned in version 1 above. Layer 3 is the "floor" of the main fluid cavity, which contains 2 (here large and rectangular) holes for fluid passage. Layer 4 contains the cavities that localize the permeable membranes, Layer 5 consists of a two separate (and different) permeable membranes. The one onto which capture molecules are immobilized prior to final assembly of the device is identical to that described in version 1 (FIGS. 1A and 2). The one at the left is for storage of the 2° reagents (e.g., Abs). Both sets of reagents are "spotted" or "striped" onto the membranes and dried prior to insertion into their respective cavities in layer 4. Layer 6 supports the permeable membranes. Layer 7 now has two separate cavities for controlling flow in the vicinity of the membranes. The one at right is identical to that in version 1, and collects all flow through the membrane to a single port. The new cavity at left delivers fluid flow to the 2° reagent storage membrane at left, as described below. Layer 8 is the floor of the device and couples to inlets and outlets for the device.

Reference is made to FIGS. 3-10 for a usage sequence for version 2 that is similar to that described above for version 1. Note that in step 4 (2° Ab loading) of version 2 (FIG. 8), the flow of fluid is up through valve 1 and the 2° Ab storage membrane and over to and down through the capture membrane. Using fluids from either valve 1 or 2, (with valve 3 open and 4 closed) flush until all excess secondary Ab is pushed through capture membrane is shown in FIG. 9. The next step is to detect (if this is Au-labeled Ab, for example) by measuring optical density of spots.

The $6^{th}$ and further steps are necessary only if using an amplification step (FIG. 10).

Representative Formats Used for Assay Development

A. 96-Well Plate Vacuum Manifold—BioDot

The BioDot vacuum manifold is suitable for testing of the flow-through immunoassays of the invention. It consists of 96 individual, open-bottom wells and a vacuum plenum that applies a low pressure below each well. Between the wells and the plenum is placed a porous membrane, patterned with capture molecules against analytes of interest. Reagents such as the sample, washing buffers, and detection molecule are added sequentially to the wells and drawn through by the applied vacuum. Pictured is an example of the assay results. Each circle in the grid lies underneath a single well and represents a unique set of assay conditions.

Figure 13:
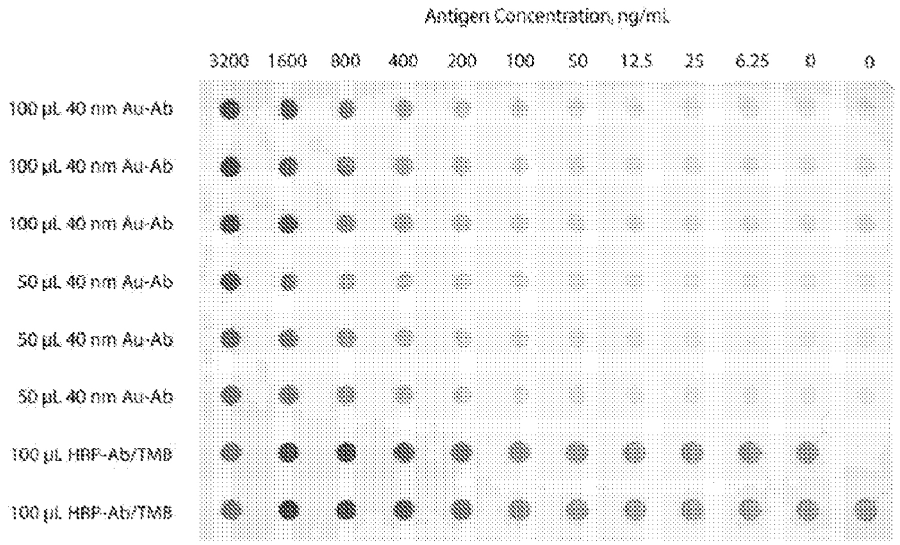
FIG. 13: Assay results showing the decrease in signal (from left to right) seen as the analyte concentration in the sample decreases. The analyte is Plasmodium falciparum Histidine-Rich Protein II, or PfHRP2. The red spots (upper 6 rows) show the results generated using an antibody-conjugated gold particle as a detection molecule; the blue spots (lower 2 rows) use an enzyme-conjugated antibody as the detection molecule, followed by an enzyme substrate that becomes a blue precipitate in the presence of the enzyme.

The assay results presented in FIG. 13 show the decrease in signal (from left to right) seen as the analyte concentration in the sample decreases. The analyte is Plasmodium falciparum Histidine-Rich Protein II, or PfHRP2. The red spots (first 6 rows) show the results generated using an antibody-conjugated gold particle as a detection molecule; the blue spots (last 2 rows) use an enzyme-conjugated antibody as the detection molecule, followed by an enzyme substrate that becomes a blue precipitate in the presence of the enzyme.

B. Mini-Vacuum

Figure 14:
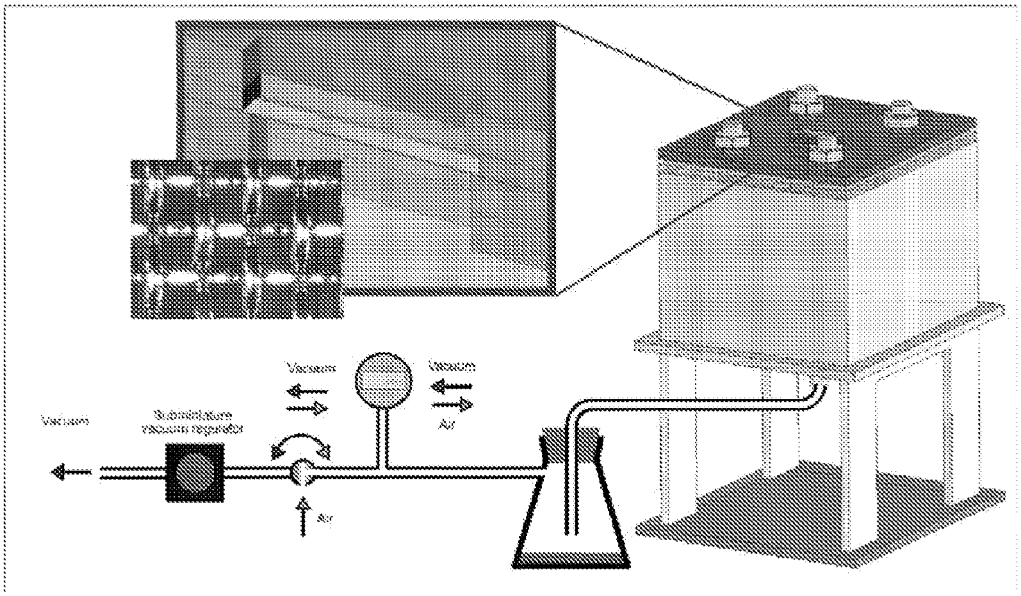
FIG. 14: Diagram of mini-vacuum format.

A similar format to the 96-well plate is the mini-vacuum or 'minivac' format. It also uses an applied vacuum to draw fluid from a reservoir through a membrane. The reservoir in this case addresses a larger area of membrane, and the membrane is supported by a metal mesh. Pictured in FIG. 14 is a diagram of the format. The mesh is depicted in the inset.

C. On-Card Assay—Dry Reagent

The assay can be run in a self-contained microfluidic format, consisting of a laminate device in which connecting fluidic channels are formed, a membrane patterned with capture molecules, a porous pad containing dried detection reagent, and an external fluid-pumping and imaging system. The multiple fluid inlets are each fed by separate pumps in this design, sidestepping the need for valves. The device is pictured in FIG. 15A-B as a diagram (15A) and photograph (15B) of the design.

With respect to FIG. 15A, the self-contained microfluidic format consists of a laminate device 150 in which connecting fluidic channels are formed by a sample loop 152 that is met by a second channel 155 delivering mobilized reagents. Their contents combine into a single channel 130 through the membrane 153. The device 150 also includes air vents 160, a membrane 153 patterned with capture molecules, a porous pad 156 containing dried detection reagent, and an external fluid-pumping and imaging system (not shown; representative example is microFlow™ System available from Micronics, Redmond, Wash.). The multiple fluid inlets include a sample inlet 151 and a second inlet 154, each fed by separate pumps in this design, sidestepping the need for valves. The second inlet 154 is used to introduce fluid that is directed to the conjugate pad 156 via second channel 155 that feeds into the sample loop 152 before it enters reaction chamber 169 and contacts the membrane 153. A bubble vent 157 can withdraw bubbles from the sample loop 152 and an outlet 158 exits the reaction chamber 169 via waste line 159.

D. On-Card Assay—Wet Reagent

Figure 17A:
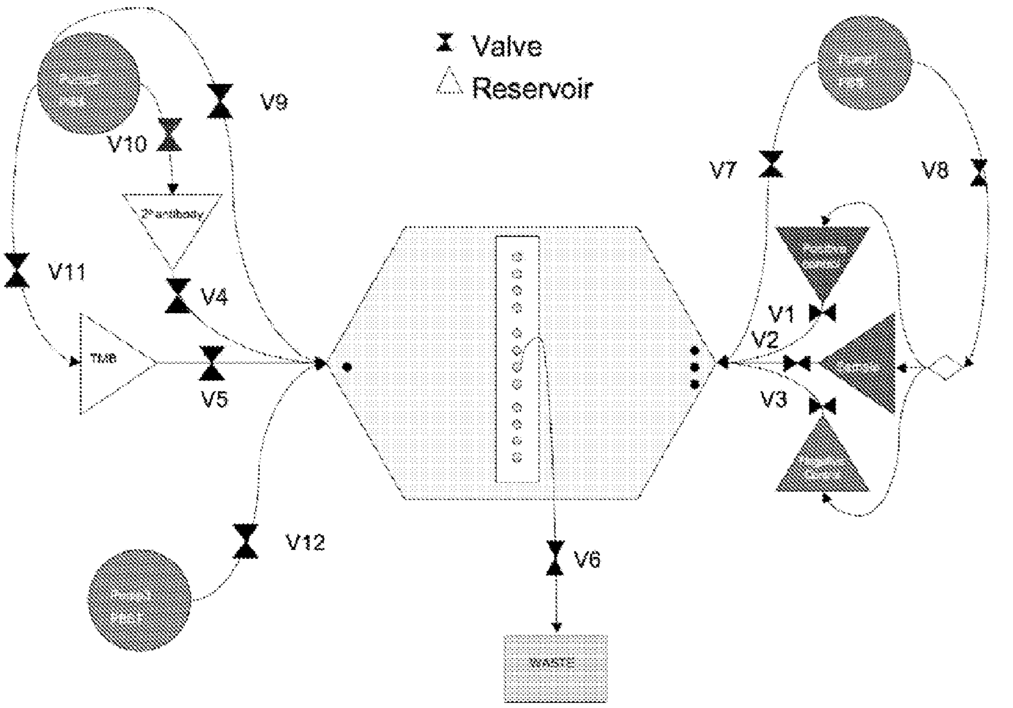
FIG. 17A: Functional schematic of assay card shown in FIG. 17B.
Figure 17B:
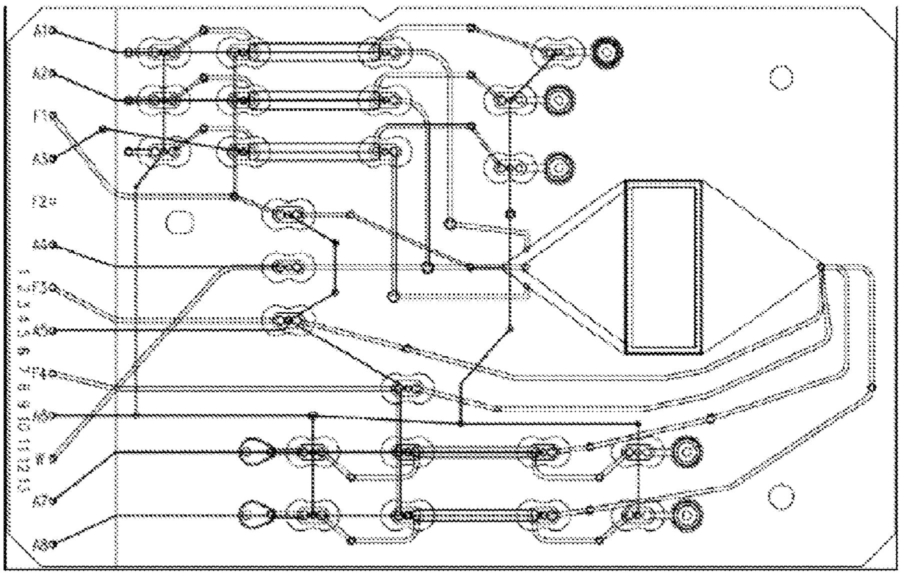
FIG. 17B: CAD design of assay card with multiple inlets to reaction chamber.

More sophisticated valved devices have been developed for controlling fluid motion from a single pump. Pictured in FIGS. 16B and 17B are two alternate designs for the assay cards. They include reagent reservoirs for liquid reagents instead of the dried reagent pads described in part C above.

FIG. 16A-B depicts a functional schematic (16A) and CAD design (16B) for assay card with single fluid inlet to the reaction chamber (the location of the assay membrane). With respect to FIG. 16B, air vents 160 are positioned in waste reservoirs 161, 162, and a bubble vent 163 is provided for priming. Valves 170 disposed throughout provide control points, such as between pipette loading vents 164 and reagent reservoirs 165-168, between pipette loading points 172 and reagent reservoirs 165-168, and between reagent reservoirs 165-168 and reaction chamber 169, as well as between pumps 174, 176 and reaction chamber 169.

FIG. 17B depicts a CAD design of assay card with multiple inlets to the reaction chamber.

Representative Results

A. Plurality of Capture Reagents Patterned on Porous Substrate

Figure 18:
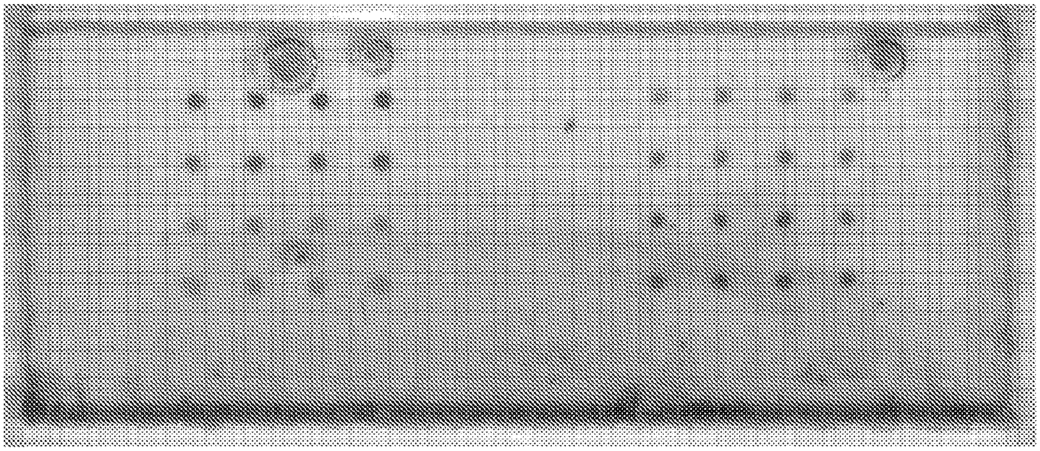
FIG. 18: Two capture reagents patterned in two 4×4 arrays on a membrane. On the left, a PfHRP2 capture molecule is patterned; on the right, an aldolase capture molecule.

Pictured in FIG. 18 is an example of two capture reagents patterned in two 4×4 arrays on a membrane. On the left, a PfHRP2 capture molecule is patterned; on the right, an aldolase capture molecule. Both PfHRP2 and aldolase were introduced to the system, followed by a gold-conjugated antibody against PfHRP2, an enzyme-conjugated antibody against aldolase, and an enzyme substrate. The PfHRP2 capture regions thus can be seen in red (left array) while the aldolase capture regions appear blue (right array). This assay was run in a simplified wet-reagent on-card assay.

B. Rehydration of Secondary Reagent Stored in Dry Form

Figure 19:
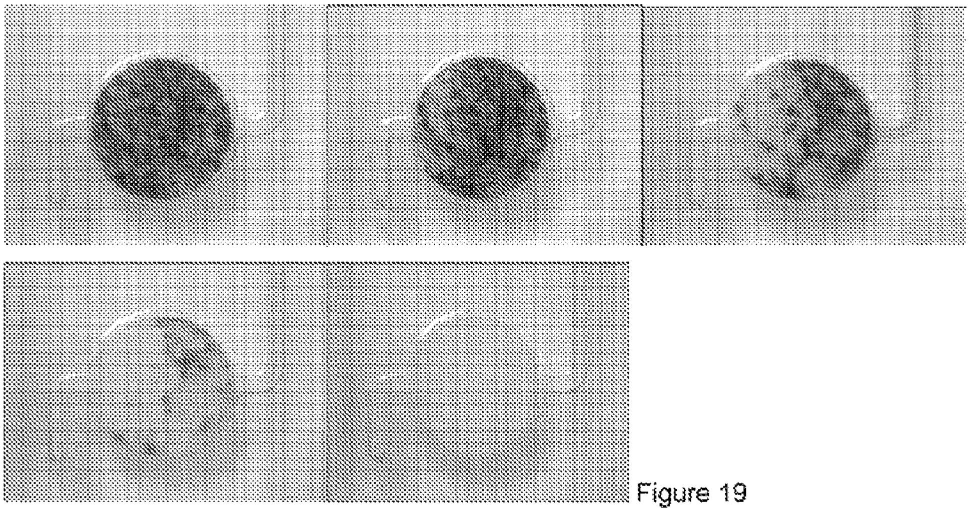
FIG. 19: Five sequential frames from a video of a dry-reagent pad being rehydrated.

Pictured in FIG. 19 are five frames from a video of a dry-reagent pad being rehydrated. Fluid moves from left to right. Apparent is the lightening of the pad to its original white color as red fluid—the dried gold-antibody conjugate—passes out the channel. The reagent's functionality is seen in the following section C.

C. Storage Depot in Communication with Assay Substrate

Following from section B above, the rehydrated gold-antibody conjugate is used in an on-card assay, using the card design pictured in FIG. 15B. In this assay, the following steps are performed:

1. Analyte-containing sample is injected into the sample loop.
2. Buffer fluid pushes the sample from the sample loop through the membrane,
3. Buffer washes unbound sample components from the membrane.
4. Buffer rehydrates the gold-antibody conjugate stored in the conjugate pad, and the air ejected is pulled into a bubble vent line.
5. Gold-antibody conjugate is passed through the membrane, binding to the captured analyte.
6. Buffer washes unbound conjugate from the membrane.

Figure 20:
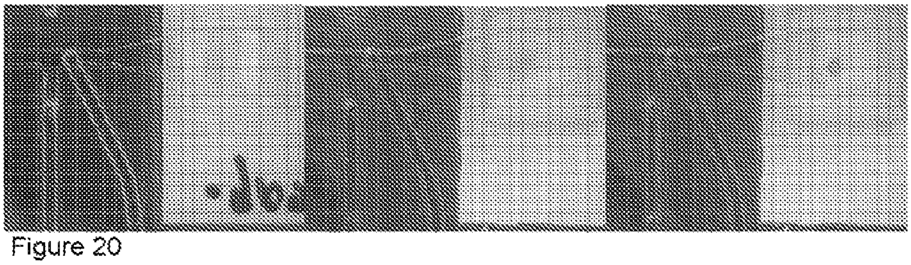
FIG. 20: Three frames from a video of an assay showing (1) sample introduction to membrane; (2) rehydrated conjugate introduced to membrane; and (3) capture spot labeled by conjugate.

Frames from a video of the assay are pictured in FIG. 20. In the first frame, sample is introduced to membrane. In the second frame, rehydrated conjugate is introduced to membrane. In the third frame, the capture spot is labeled by conjugate.

D. Optical Detection of Assay Results

Figure 21:
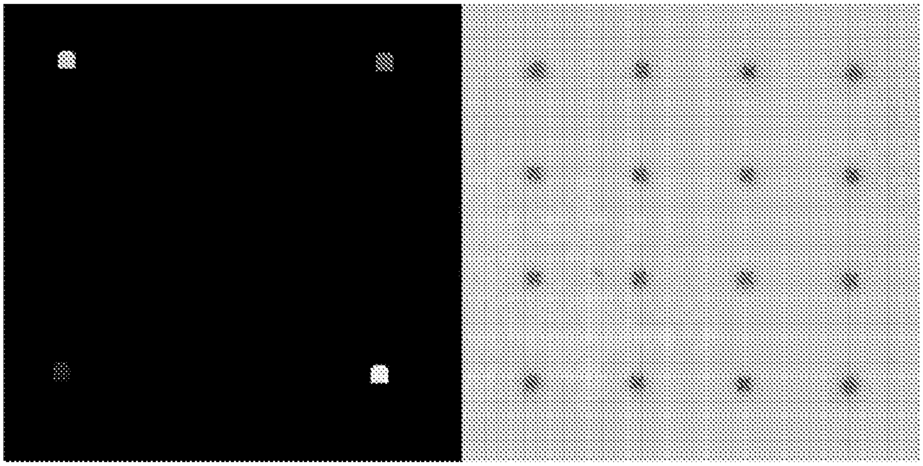
FIG. 21: Images indicating steps of automated optical measurement. On the left, four separate registration marks are identified in an image; on the right, the analyzed image (captured by a flatbed scanner, 48-bit RGB, 3200 dpi) with simulated blue registration marks and red assay spots, the location of each marked with an X.

Optical measurement of assay results has been performed using several methods. Images have been captured by both a flatbed scanner (48-bit RGB, 3200 dpi) and a USB "webcam." The assay results from captured images can be quantified by measuring the pixel count in one or more of the color channels. This measurement has been assisted by a semi-automated measurement process that involves user-selection of several reference spots in a grid of assay capture regions, followed by automated detection of the other spots in the grid. Additionally, it is possible to automatically detect registration marks such as the blue dots (4 corners on right array of FIG. 21), and then use these locations to define the locations of the assay spots of interest. The image here shows the four detected registration marks and the 12 detected assay spots (each marked with an "x"). The intensity of the spot correlates with the amount of analyte present in the sample.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An assay device for detection of an analyte in a fluidic sample, the device comprising:

(a) a microfluidic chamber comprising a single fluidic channel having a first inlet, an outlet, and an axis;

(b) a first surface in communication with the first inlet and the outlet, wherein the first surface is disposed within the single fluidic channel and wherein the first surface comprises a plurality of capture regions, wherein the capture regions are upstream of the outlet;

(c) a plurality of capture agents immobilized on the first surface within the capture regions, wherein the capture agents specifically bind the analyte;

(d) a reagent storage depot in communication via a the single fluidic channel with the first surface, wherein the storage depot is disposed within the single fluidic channel and wherein the storage depot comprises a plurality of reagent regions aligned with corresponding capture regions;

(e) a first valve disposed between the storage depot and the capture regions; and, (f) a plurality of detection reagents that specifically bind the analyte and that become mobile upon contact with fluid, wherein the detection reagents are disposed within the reagent regions, and wherein fluid traverses from the plurality of reagent regions to corresponding capture regions in parallel with the axis of the single fluidic channel.

2. The device of claim 1, wherein the first surface comprises a porous carrier.

3. The device of claim 1, wherein the storage depot comprises one or more cavities.

4. The device of claim 1, wherein the storage depot comprises a polymeric compound immobilized on the device.

5. The device of claim 1, wherein the storage depot comprises a porous membrane.

6. The device of claim 1, further comprising a second inlet in communication with the storage depot.

7. The device of claim 1, wherein the capture agents and the detection reagents are in dry form.

8. The device of claim 1, which comprises a plurality of polymeric layers.

9. The device of claim 6, further comprising a second valve disposed between the second inlet and the first surface and/or between the second inlet and the storage depot.

10. A method of detecting the presence of an analyte in a fluidic sample, the method comprising:

(a) delivering a fluidic sample into the first inlet of a device of claim 1 under conditions permitting contact between the sample and the capture agents immobilized on the first surface;

(b) contacting a single stream of fluid with the plurality of detection reagents under conditions effecting migration of the detection reagents to the first surface;

(c) detecting the presence of detection reagent bound to analyte that is bound to the immobilized capture agents, whereby presence of detection reagent is indicative of the presence of the analyte.

11. The method of claim 10, wherein the delivering of step (a) comprises pumping the fluidic sample into the first inlet.

12. The method of claim 10, further comprising delivering one or more control samples via laminar flow into the first inlet.

13. The method of claim 12, wherein step (a) comprises delivering one stream of a test fluidic sample, one stream of a positive control fluidic sample, and one stream of a negative control fluidic sample.

14. The method of claim 12, wherein the streams of fluidic sample are delivered via a single channel.

15. The method of claim 12, wherein the streams of fluidic sample are delivered via separate channels.

16. The method of claim 10, wherein the contacting of step (b) comprises pumping fluid into a second inlet that is in communication with the reagent storage depot.

17. The method of claim 10, wherein the delivering of step (a) provides the contacting of step (b), whereby the fluidic sample, upon contact with the detection reagents, effects migration of the detection reagents.

18. The method of claim 10, wherein the capture agents and the detection reagents comprise antibodies and/or antigens.

19. The method of claim 10, wherein the contacting of step (b) further comprises delivering to the first surface an amplification reagent that binds to the detection reagents.

20. The method of claim 10, wherein the detecting comprises measuring an optical property selected from optical absorbance, reflectivity, optical transmission, chemiluminescence or fluorescence.

21. The device of claim 1, wherein the plurality of reagent regions is aligned in parallel with the plurality of capture regions and perpendicular to the axis of the single fluidic channel.

22. The device of claim 1, wherein the reagent regions comprise differing detection reagents that travel in parallel when fluid traverses from the plurality of reagent regions to the corresponding capture regions under laminar flow conditions.

* * * * *

UNITED STATES PATENT AND TRADEMARK OFFICE

CERTIFICATE OF CORRECTION

PATENT NO. : 8,101,403 B2
APPLICATION NO. : 12/444385
DATED : January 24, 2012
INVENTOR(S) : Paul Yager et al.

It is certified that error appears in the above-identified patent and that said Letters Patent is hereby corrected as shown below:

On Title page 2, Item (56) column 1, under the head *Foreign Patent Documents* insert the following:

| | | |
|---|---|---|
| --KR | 10-2000-0036176 | 06/2000 |
| WO | WO/03038436 | 05/2003-- |

At Column 12, line 10, after via, delete “a”

Signed and Sealed this
Thirteenth Day of March, 2012

David J. Kappos

David J. Kappos
*Director of the United States Patent and Trademark Office*